United States Patent [19]
Kume et al.

[11] Patent Number: 5,876,426
[45] Date of Patent: Mar. 2, 1999

[54] SYSTEM AND METHOD OF PROVIDING A BLOOD-FREE INTERFACE FOR INTRAVASCULAR LIGHT DELIVERY

[75] Inventors: Stewart M. Kume, Plymouth; Thomas R. Hektner, Medina, both of Minn.

[73] Assignee: Scimed Life Systems, Inc., Maple Grove, Minn.

[21] Appl. No.: 662,585

[22] Filed: Jun. 13, 1996

[51] Int. Cl.⁶ .................................................. A61M 29/00
[52] U.S. Cl. ............................... 607/88; 607/92; 606/14; 606/194; 604/96
[58] Field of Search ........................ 604/19–21, 96–104; 606/191–200, 13–16; 607/88, 89, 92

[56] References Cited

U.S. PATENT DOCUMENTS

| | | |
|---|---|---|
| Re. 34,544 | 2/1994 | Spears . |
| 4,040,413 | 8/1977 | Ohshiro . |
| 4,224,929 | 9/1980 | Furihata . |
| 4,331,132 | 5/1982 | Mukasa . |
| 4,336,809 | 6/1982 | Clark . |
| 4,445,892 | 5/1984 | Hussein et al. . |
| 4,470,407 | 9/1984 | Hussein . |
| 4,512,762 | 4/1985 | Spears . |
| 4,527,549 | 7/1985 | Gabbay ................................... 604/101 |
| 4,619,247 | 10/1986 | Inoue et al. . |
| 4,676,231 | 6/1987 | Hisazumi . |
| 4,681,093 | 7/1987 | Ono et al. . |
| 4,762,120 | 8/1988 | Hussein . |
| 4,770,653 | 9/1988 | Shturman . |
| 4,773,899 | 9/1988 | Spears . |
| 4,779,611 | 10/1988 | Grooters et al. . |
| 4,782,818 | 11/1988 | Mori . |
| 4,784,133 | 11/1988 | Mackin . |
| 4,795,458 | 1/1989 | Regan . |
| 4,799,479 | 1/1989 | Spears . |
| 4,808,164 | 2/1989 | Hess . |
| 4,852,567 | 8/1989 | Sinofsky . |

(List continued on next page.)

FOREIGN PATENT DOCUMENTS

| | | |
|---|---|---|
| 94109858 | 6/1994 | European Pat. Off. . |
| 0552189 | 3/1995 | European Pat. Off. . |
| WO 90/00914 | 2/1990 | WIPO . |
| 92/07623 | 5/1992 | WIPO . |
| 95/07667 | 3/1995 | WIPO . |

OTHER PUBLICATIONS

"More Brightness for Excellence in Intraluminal Diagnostics!" 8–pg. Brochure from Ad Krauth.

"Lasers in Cardiovascular Medicine and Surgery: Fundamentals and Techniques," G. Abela, M.D., Kluwer Academic Publishers, pp. 399–422, 1990.

*Primary Examiner*—Danton D. DeMille
*Assistant Examiner*—David M. Ruddy
*Attorney, Agent, or Firm*—Robert E. Atkinson

[57] ABSTRACT

A system and method of providing a blood-free interface for intravascular light delivery is disclosed. The method includes the steps of inserting a balloon catheter into the vasculature of a patient wherein the balloon catheter includes an infusion layer disposed about the balloon; inserting a light delivery catheter into the working lumen of the balloon catheter; inflating the balloon to displace blood inside the vasculature; infusing a liquid to displace blood between the inflated balloon and the inside wall of the vasculature so as to provide a relatively blood-free interface; and delivering light through the blood-free interface to the vasculature from the light delivery catheter. Fluid may be infused into the working lumen of the balloon catheter and around the light delivery catheter in order to displace any blood in the lumen. The system includes a light delivery catheter and a balloon catheter where the balloon catheter includes a long shaft having an inflation lumen, an infusion lumen and a working lumen. A balloon is connected to the distal end of the shaft and an infusion layer is disposed about the balloon. The catheter may include one or more radial restraints disposed about the balloon to center the working lumen and to limit the expandable diameter of the balloon. The radial restraint imparts flexibility and allows the balloon and the working lumen to be centered in vasculature that is curved (i.e., non-linear).

6 Claims, 3 Drawing Sheets

U.S. PATENT DOCUMENTS

| | | |
|---|---|---|
| 4,862,874 | 9/1989 | Kellner . |
| 4,878,492 | 11/1989 | Sinofsky et al. . |
| 4,878,725 | 11/1989 | Hessel et al. . |
| 4,886,496 | 12/1989 | Conoscenti et al. . |
| 4,892,099 | 1/1990 | Ohkawa et al. . |
| 4,917,084 | 4/1990 | Sinofsky . |
| 4,921,484 | 5/1990 | Hillstead . |
| 4,927,413 | 5/1990 | Hess . |
| 4,950,266 | 8/1990 | Sinofsky . |
| 4,961,738 | 10/1990 | Mackin . |
| 4,976,710 | 12/1990 | Mackin . |
| 4,994,060 | 2/1991 | Rink et al. . |
| 5,007,898 | 4/1991 | Rosenbluth et al. . |
| 5,019,042 | 5/1991 | Sahota ..................................... 604/101 |
| 5,019,075 | 5/1991 | Spears et al. . |
| 5,029,574 | 7/1991 | Shimamura . |
| 5,029,588 | 7/1991 | Yock et al. . |
| 5,030,227 | 7/1991 | Rosenbluth et al. . |
| 5,036,463 | 7/1991 | Abela et al. . |
| 5,042,980 | 8/1991 | Baker et al. . |
| 5,053,033 | 10/1991 | Clarke . |
| 5,071,417 | 12/1991 | Sinofksy . |
| 5,071,429 | 12/1991 | Pinchuk et al. . |
| 5,078,681 | 1/1992 | Kawaxhima . |
| 5,090,959 | 2/1992 | Samson et al. . |
| 5,092,841 | 3/1992 | Spears . |
| 5,100,429 | 3/1992 | Sinofsky et al. . |
| 5,103,804 | 4/1992 | Abele et al. . |
| 5,116,317 | 5/1992 | Carson et al. . |
| 5,117,831 | 6/1992 | Jang et al. . |
| 5,125,925 | 6/1992 | Lundahl . |
| 5,152,277 | 10/1992 | Honda et al. . |
| 5,159,920 | 11/1992 | Condon et al. . |
| 5,162,950 | 11/1992 | Suman et al. . |
| 5,163,935 | 11/1992 | Black et al. . |
| 5,163,950 | 11/1992 | Pinchuk et al. . |
| 5,167,233 | 12/1992 | Eberle et al. . |
| 5,169,395 | 12/1992 | Narciso ..................................... 604/21 |
| 5,188,596 | 2/1993 | Condon et al. . |
| 5,196,004 | 3/1993 | Sinofsky . |
| 5,196,005 | 3/1993 | Doiron et al. . |
| 5,199,951 | 4/1993 | Spears . |
| 5,201,317 | 4/1993 | Kanazawa et al. . |
| 5,203,337 | 4/1993 | Feldman . |
| 5,207,669 | 5/1993 | Baker et al. . |
| 5,209,748 | 5/1993 | Daikuzono . |
| 5,213,580 | 5/1993 | Slepian et al. . |
| 5,242,438 | 9/1993 | Saadatmanesh et al. . |
| 5,248,311 | 9/1993 | Black et al. . |
| 5,254,112 | 10/1993 | Sinofsky et al. . |
| 5,257,970 | 11/1993 | Dougherty . |
| 5,263,928 | 11/1993 | Trauthen et al. . |
| 5,292,305 | 3/1994 | Boudewijn et al. . |
| 5,293,872 | 3/1994 | Alfano et al. . |
| 5,295,962 | 3/1994 | Crocker et al. ......................... 604/101 |
| 5,330,467 | 7/1994 | Abela . |
| 5,344,419 | 9/1994 | Spears . |
| 5,370,608 | 12/1994 | Sahota et al. . |
| 5,409,483 | 4/1995 | Campbell et al. . |
| 5,417,653 | 5/1995 | Sahota et al. . |
| 5,441,497 | 8/1995 | Narcisco, Jr. . |
| 5,453,448 | 9/1995 | Narciso ..................................... 604/21 |
| 5,456,661 | 10/1995 | Narciso, Jr. . |
| B1 4,733,665 | 1/1994 | Palmaz . |

SYSTEM AND METHOD OF PROVIDING A BLOOD-FREE INTERFACE FOR INTRAVASCULAR LIGHT DELIVERY

CROSS-REFERENCE TO RELATED APPLICATIONS

This application is related to U.S. patent application Ser. No. 08/432,318 filed on May 1, 1995, entitled METHODS OF USING AN INTRAVASCULAR BALLOON CATHETER IN COMBINATION WITH AN ANGIOSCOPE, which is a continuation-in-part of U.S. Pat. No. 5,411,016 to Kume et al., entitled INTRAVASCULAR BALLOON CATHETER FOR USE IN COMBINATION WITH AN ANGIOSCOPE, the entire disclosures of which are hereby incorporated by reference.

FIELD OF THE INVENTION

The present invention generally relates to medical devices. More specifically, the present invention relates to devices and methods for intralumenal light delivery. Those skilled in the art will recognize the benefits of applying the present invention to similar fields not discussed herein.

BACKGROUND OF THE INVENTION

Coronary artery disease is commonly treated by relatively non-invasive techniques such as percutaneous translumenal coronary angioplasty (PTCA). Conventional PTCA is well known in the art and typically involves the use of a balloon catheter, possibly in combination with other intravascular devices such as a guide wire and a guide catheter. A typical balloon catheter has an elongate shaft with a balloon attached to its distal end and a manifold attached to its proximal end. In use, the balloon catheter is advanced into a guide catheter and over a guide wire such that the balloon is positioned adjacent a restriction in a diseased coronary artery. The balloon is then inflated and the restriction in the vessel is opened.

A common problem with PTCA is the occurrence of restenosis in approximately one-third to one-half of the patients treated, depending on the condition of the vessel being treated. Various therapies have been proposed to treat restenosis. For example, some types of light have been suggested as a means to prevent restenosis of a previously dilated vascular restriction. U.S. Pat. No. 5,417,653 to Sahota et al. discloses a method of preventing restenosis by delivering light utilizing a balloon catheter. The balloon described in Sahota '653 serves both to dilate the stenosis and to displace blood from the treatment site. Since blood is relatively opaque to UV light, displacing blood from the treatment site is important for treating the vascular wall with UV light. A significant problem with the method described in Sahota '653 is that blood becomes trapped between the outside surface of the inflated balloon and the inside surface of the vascular wall. Since blood is relatively opaque to UV light, the trapped blood prevents effective treatment of the vascular site.

Utilizing a "weeping balloon" as described in U.S. Pat. No. 5,087,244 to Wolinsky has been suggested as a method of eliminating the blood trapped between the outside surface of the inflated balloon and the inside surface of the vascular wall. However, this system does not allow the balloon to be inflated independently of infusing fluid around the balloon. This is a significant disadvantage because it is not considered desirable to infuse at the relatively higher balloon inflation pressure. Infusing at such a high pressure may result in excessive infusion flow rates, damage to the vessel wall and/or life threatening dissections. In addition, the balloon diameter cannot be controlled independently of the infusion rate if a compliant balloon is used.

SUMMARY OF THE INVENTION

The present invention overcomes the disadvantages of the prior art by providing a system and method for creating a blood-free interface for intravascular light delivery. In particular, the present invention provides, inter alia, a system and method to dilate a stenosis and uniformly delivery light to a vascular wall through a blood-free interface for diagnostic or therapeutic purposes.

One aspect of the present invention may be described as a method of providing a blood-free interface for intravascular light delivery wherein the method includes the steps of (1) providing a balloon catheter having a balloon, an infusion layer and a working lumen; (2) providing a light delivery catheter; (3) inserting the balloon catheter into the vasculature of a patient; (4) inserting the light delivery catheter into the working lumen of the balloon catheter; (6) inflating the balloon to displace blood inside the vasculature; (7) infusing a liquid to displace blood between the inflated balloon and the inside wall of the vasculature so as to provide a relatively blood-free interface; and (8) delivering light through the blood-free interface to the vasculature from the light delivery catheter. Fluid may be infused into the working lumen of the balloon catheter and around the light delivery catheter in order to displace any blood in the lumen.

The light delivery catheter may be inserted into the working lumen of the balloon catheter either prior to, subsequent to or simultaneous with inserting the balloon catheter into the vasculature. In addition, the balloon may be inflated either prior to, subsequent to or simultaneous with infusing the fluid to create a blood-free interface.

Another aspect of the present invention may be described as a system for providing a blood-free interface for intravascular light delivery where the system includes a light delivery catheter and a balloon catheter. The balloon catheter includes a long shaft having an inflation lumen, an infusion lumen and a working lumen. A balloon is connected to the distal end of the shaft and defines an interior which is in fluid communication with the inflation lumen. An infusion layer is disposed about the balloon to define an infusion space therebetween which is in fluid communication with the infusion lumen. The balloon catheter may include one or more radial restraints disposed about the balloon to limit the expandable diameter of the balloon such that the working lumen remains centered in a curved (i.e., non-linear) vascular path and such that the inflated balloon is more flexible.

Yet another aspect of the present invention may also be described as a balloon catheter for providing a blood-free interface for intravascular light delivery wherein the catheter includes a shaft having an inflation lumen, an infusion lumen and a working lumen. A balloon is connected to the distal end of the shaft and an infusion layer is disposed about the balloon. Fluid may be infused around the inflated balloon to displace blood trapped between the outside surface of the balloon and the inside surface of the vasculature. A radial restraint is disposed about a mid-portion of the balloon to limit the expandable diameter of the balloon. The radial restraint allows the balloon and the working lumen to be centered in vasculature that is non-linear and imparts flexibility in the inflated balloon. One or more radial restraints may be used.

Other aspects and advantages of the present invention can be fully appreciated with a thorough review of the entire specification and drawings. Those skilled in the art will appreciate other advantages not fully described herein. Furthermore, while the disclosure focuses on balloon catheters, those skilled in the art will recognize that the invention may be incorporated into other devices and methods of use without departing from the spirit of the invention.

DETAILED DESCRIPTION OF THE INVENTION

The following detailed description should be read with reference to the drawings in which similar parts in different drawings are numbered the same. The drawings, which are not necessarily to scale, depict exemplary embodiments and are not intended to limit the scope of the invention.

Examples of materials, dimensions, assemblies and manufacturing processes are provided for selected parts. All other parts employ that which is known to those skilled in the field of the invention. Those skilled in the art will recognize that many of the examples provided have suitable alternatives which may also be utilized.

Figure 1:
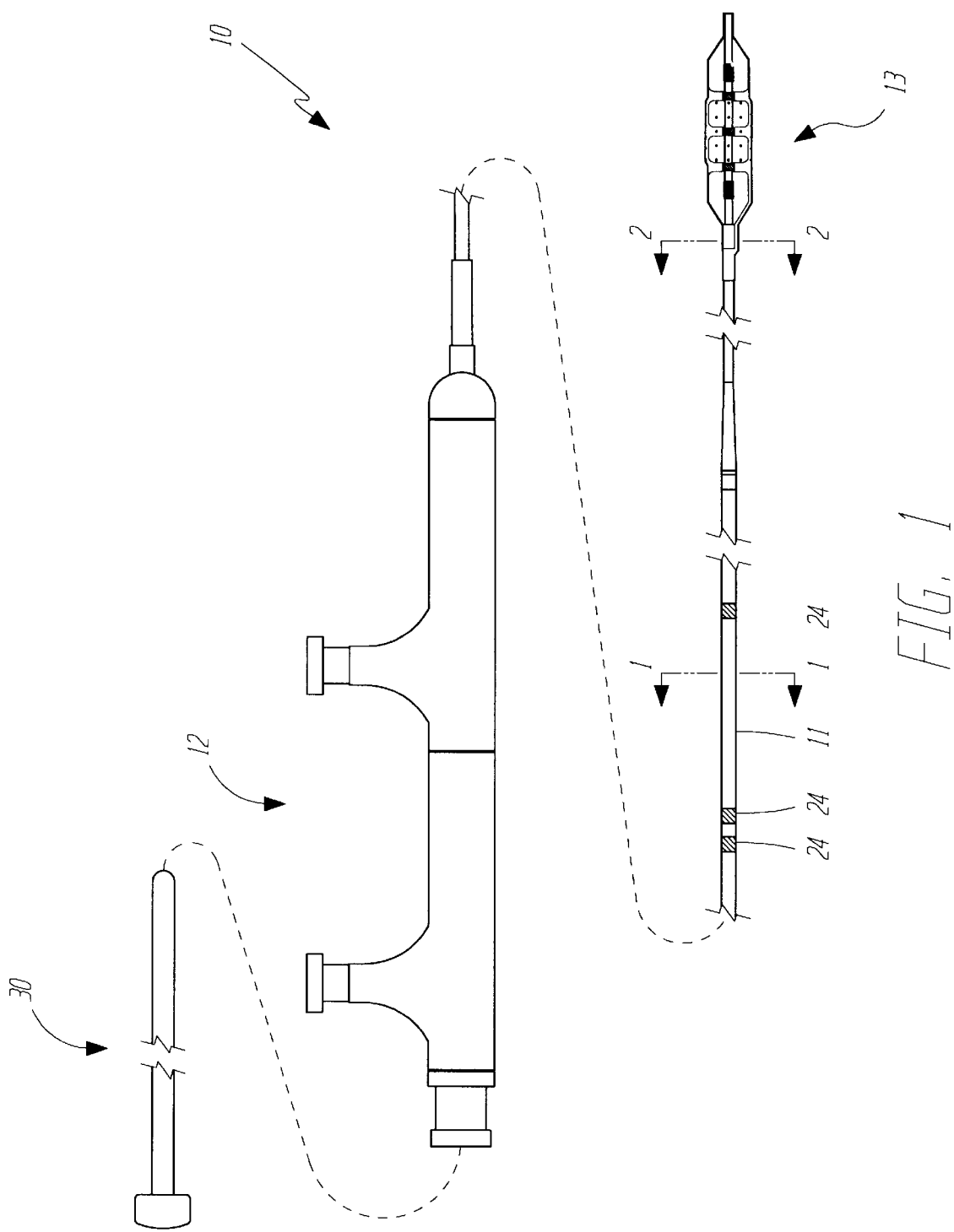
FIG. 1 is a profile side view of the balloon catheter of the present invention.

Refer to FIG. 1 which illustrates balloon catheter 10 of the present invention. Except as discussed hereinafter, catheter 10 may be made as described in U.S. Pat. No. 5,295,962 to Crocker et al., the entire disclosure of which is incorporated herein by reference.

Figure 3:
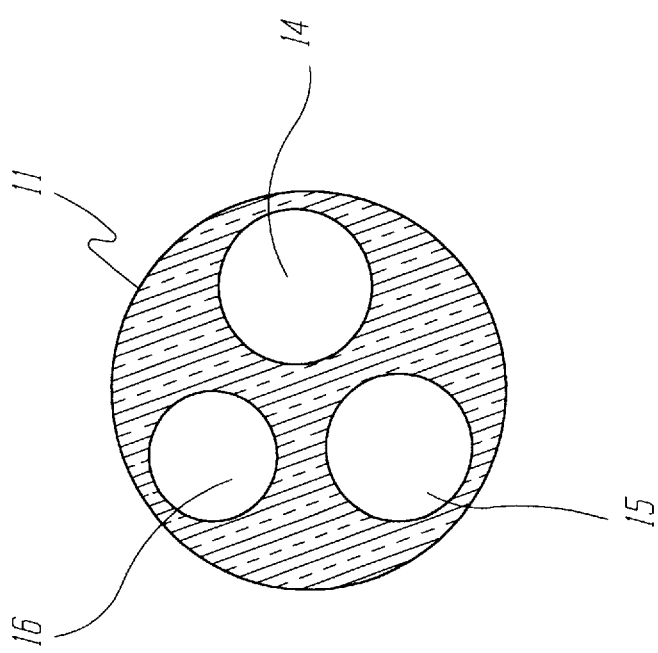
FIG. 3 is a cross-sectional view taken at 1—1 in FIG. 1.

Catheter 10 includes an elongate shaft 11 having a proximal end and a distal end. A manifold assembly 12 is connected to the proximal end of the shaft 11 and a balloon assembly 13 is connected to the distal end of the shaft 11. In addition light delivery catheter 30 may be inserted into catheter 10. As best illustrated in FIG. 3, shaft 11 includes a guide wire/working lumen 14, an infusion lumen 15 and an inflation lumen 16. Each lumen 14,15,16 has a corresponding access port included in the manifold assembly 12.

Elongate shaft 11 may be formed of a multilumen polymer (e.g., polyethylene) extrusion having a length on the order of 135 cm, a proximal outside diameter of about 0.046 inches and a distal outside diameter of about 0.037 inches. The guide wire/working lumen 14 may have a diameter of about 0.017 inches or larger to accommodate both guide wires and light delivery catheters. The shaft 11 may be formed of a single tube or the shaft 11 may be formed by thermally bonding a proximal shaft portion and a reduced diameter distal shaft portion. Proximal shaft marks 24 may be incorporated onto the shaft 11 to aid in catheter placement.

Figure 2:
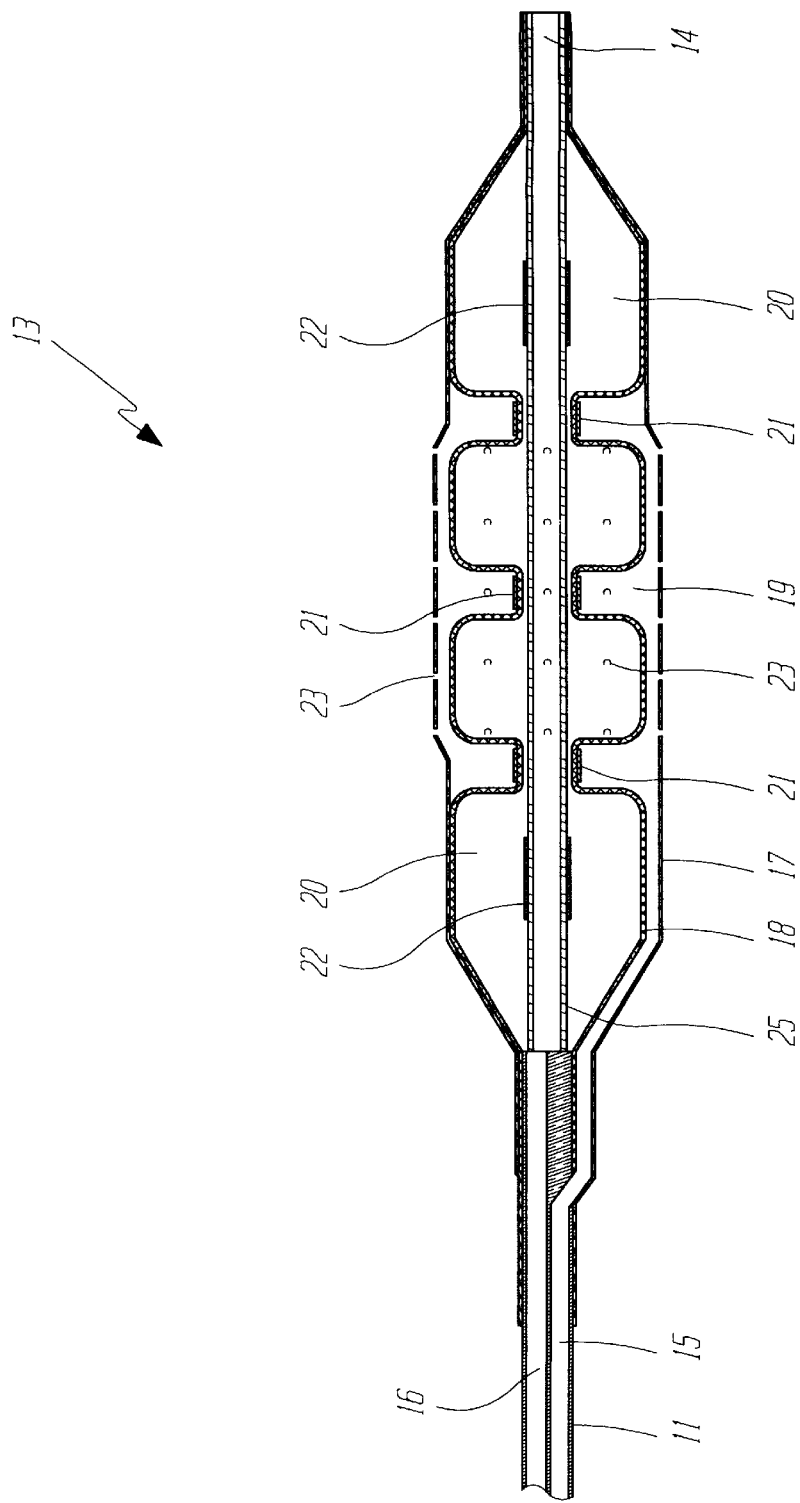
FIG. 2 is a cross-sectional side view of the distal end of the balloon catheter illustrated FIG. 1.
Figure 4:
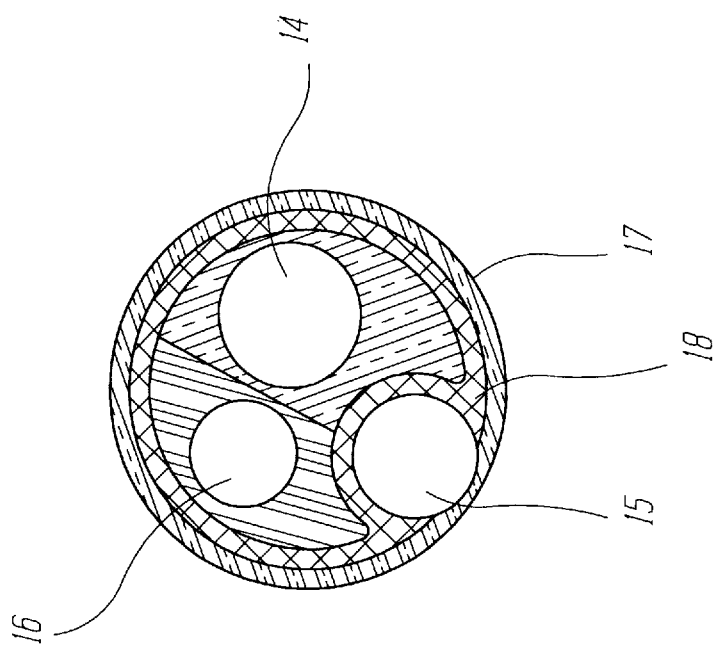
FIG. 4 is a cross-sectional view taken at 2—2 in FIG. 1.

Refer now to FIG. 2 which illustrates the balloon assembly 13 of the balloon catheter 10. Balloon assembly 13 includes an infusion layer 17 disposed about a dilatation balloon 18. A balloon interior 20 is defined inside the balloon 18 and may be segmented by restriction bands 21. The restriction bands 21 center the working lumen 14 even in a non-linear vascular path. In addition, the restriction bands 21 prevent the balloon 18 from fully inflating and thereby create flex points which allow the balloon assembly 13 to conform to curved vasculature while keeping the guide wire tube 25 relatively centered. An infusion space 19 is defined between the outside surface of the balloon 18 and the inside surface of the infusion layer 17. The infusion lumen 15 and the inflation lumen 16 are in fluid communication with the infusion space 19 and the balloon interior 20, respectively. Several infusion holes or perforations 23 are formed in the infusion layer 17 such that fluid may pass through from the infusion space 19 to the exterior of the balloon assembly 13. Two marker bands 22 may be placed on the guide wire tube 25 in order to facilitate radiographic visualization.

Infusion layer 17 and balloon 18 may be formed of a blow-molded polymer such as polyethylene-ethylvinylacetate copolymer. The proximal ends of the infusion layer 17 and the balloon 18 may be thermally or adhesively bonded to the shaft 11. The distal ends of the infusion layer 17 and the balloon 18 may be thermally or adhesively bonded to the guide wire tube 25. When the balloon 18 is inflated, the profile of the balloon assembly 13 may range from about 2.0 mm to about 10.0 mm and the working length may range from about 10 mm to about 40 mm. Approximately 40 holes 23 having a diameter of about 0.008 to 0.010 inches spaced uniformly about the infusion layer 17 has been found to adequately remove blood trapped between the inflated balloon assembly 13 and the inside surface of the vessel. The holes 23 may be formed by mechanical or laser drilling, or by using punch and die process.

The balloon assembly 13 may be made by molding the balloon 18, molding the infusion layer 17, preparing the distal end of the shaft 11, preparing the guide wire tube 25 and assembling the various components. The following is a detailed example of how the balloon assembly 13 may be made.

To make the balloon 18, a balloon tube is selected depending on the desired size of the balloon 18 to be made. The ends of the tube are cut at angles using a conventional razor blade and restriction bands 21 are slid onto the tube. The restriction bands 21 may be formed of polyimide having a wall thickness of about 0.001 to 0.003 inches and an inside diameter sufficient to permit fluid to flow between the inside surface of the balloon 18 and the outside surface of the guide wire tube 25. Preferably three restriction bands 21 are uniformly spaced on the balloon tube at a distance of about 4.0 to 10.0 mm leaving sufficient space both proximal and distal of the balloon tube for later processing. The balloon tube with the restriction rings 21 thereon may be heated and blow molded in a PTFE tube to the desired length and diameter. The restriction bands 21 may be removed if the molded balloon has sufficient integrity to maintain the restrictions during inflation. This may be necessary if the bands 21 would otherwise be opaque to the radiation delivered. The infusion layer 17 may be formed by essentially the same process except that no restriction rings are necessary.

The distal end of the shaft 11, in the form of a three-lumen extrusion, may be prepared by first inserting mandrels into each of the three lumens. The guide wire lumen 14 is then skived at an angle approximately 8.0 to 10.0 mm proximal of the distal end of the shaft 11. The skived portion is then removed along with the mandrel and a PTFE capture sleeve is placed on the shaft 11 just proximal of the skive. A cut-to-length polyethylene guide wire tube 25 is placed over a PTFE mandrel and the mandrel is slid into the distal end of the guide wire lumen 14 in the shaft 11. Radiopaque marker bands 22 are secured to the guide wire tube 25 using a suitable medical grade adhesive.

The molded balloon 18 is then placed over the distal end of the shaft 11 and guide wire tube 25 until the proximal end of the balloon 18 is proximal of the skived guide wire lumen 14. The proximal end of the balloon 18 is thermally bonded to the shaft 11 and to the guide wire tube 25 thus providing a fluid tight seal. The proximal thermal bond also functions to connect the guide wire tube 25 to the distal end of the shaft 11. The proximal end of the balloon 18 and the proximal end of the infusion layer 17 are thermally tacked together with the PTFE bead disposed therein. Thermally tacking the balloon 18 to the infusion layer 17 is important to facilitate full collapse of the infusion layer 17 when the balloon 18 is deflated. The PTFE bead is then removed and the distal end of the balloon 18 is thermally bonded to the distal end of the guide wire tube 25 to fluidly seal the balloon interior 20. The distal end of the balloon 18 and the distal end of the infusion layer 17 are then thermally tacked together. Alternatively, the balloon 18 and the infusion layer 17 may be thermally tacked prior to making the distal seal. Once sealed, the distal end of the balloon 18 and the distal end of the guide wire tube 25 may be trimmed to length.

A skive having a length of about 3 to 5 mm is then cut into the infusion lumen 15 adjacent the proximal end of the balloon 18. With a PTFE bead inserted into the infusion lumen 15 and extending out of the skived opening, the infusion layer 17 is slid over the balloon 18 and the proximal end of the infusion layer 17 is thermally bonded to the shaft 11 proximal of the skived opening.

The PTFE capture sleeve previously placed over the shaft 11 is slid distally and positioned over the proximal end of the infusion layer 17. While the sleeve is in position, it is exposed to heat such that the sleeve shrinks onto the proximal bond site and forms a smooth, low profile connection. After cooling, the capture sleeve is removed and the same procedure is performed on the distal bond site. After removing the remaining mandrels, the balloon assembly 13 is inspected for proper assembly.

The preceding method of making the balloon assembly 13 is exemplary only and those skilled in the art will recognize that other manufacturing methods may also be employed.

In use, the catheter 10 may be used to provide a blood-free interface for intravascular light delivery. The light delivered utilizing catheter 10 may be for therapeutic or diagnostic purposes. In addition, the catheter 10 may be used independently (e.g., dilation and/or drug delivery and/or photo-activated drug delivery with subsequent UV light treatment) or as an adjunct device (e.g., as a follow-up to an atherectomy procedure).

The following is an example of how catheter 10 may be used. The example assumes the device is used as the primary therapeutic/diagnostic tool but catheter 10 may be used as an adjunct device as mentioned previously.

Once vascular access is established, the catheter 10 may be advanced to the treatment site. To navigate the catheter 10 to the treatment site, a guide wire or light guide (not shown) may be employed in the guide wire/working lumen 14. The catheter 10 and the guide wire may be advanced simultaneously or the catheter 10 may be advanced over a previously inserted guide wire. If a guide wire is used, it may be necessary to remove the guide wire so that a light guide or a light delivery catheter may be inserted into the guide wire/working lumen 14.

Once the catheter 10 is in the desired position, the balloon 18 may be inflated to dilate the restriction. If no dilatation is necessary, the balloon 18 may be inflated simply to displace blood from the treatment site. With the balloon 18 inflated, fluid may be infused through the infusion layer 17 in order to displace blood between the inflated balloon and the inside wall of the vasculature so as to provide a relatively blood-free interface. Note that fluid may be infused prior to, simultaneously with or subsequent to inflating the balloon 18. In addition, fluid may be infused into the working lumen of the balloon catheter and around the light delivery catheter in order to displace any blood in the lumen. Once a blood-free interface is established, a diffusing tipped light guide/light delivery catheter or other suitable light delivery system (not shown) may be used to deliver light from the guide wire/working lumen 14, through the guide wire tube 25, through the balloon interior 20 (which is filled with fluid), through the balloon 18, through the infusion space 19 (which is also filled with fluid), through the infusion layer 17 and across the blood-free interface to the treatment site. After light is delivered to the treatment site, subsequent diagnostic or therapeutic procedures may be performed as deemed appropriate by the treating physician.

While the specification describes the preferred constructions, materials, dimensions, methods of manufacture and methods of practice, those skilled in the art will appreciate the scope and spirit of the invention with reference to the appended claims.

What is claimed is:

1. A method of providing a blood-free interface for intravascular light delivery, the method comprising the steps of:
 a. providing a balloon catheter, the balloon catheter including:
  i. an elongate shaft having an inflation lumen, an infusion lumen and a working lumen;
  ii. a balloon connected to the distal end of the shaft, the balloon defining an interior which is in fluid communication with the inflation lumen; and
  iii. an infusion layer disposed about the balloon to define an infusion space therebetween which is in fluid communication with the infusion lumen;
 b. providing a light delivery catheter;
 c. inserting the balloon catheter into the vasculature of a patient;
 d. inserting the light delivery catheter into the working lumen of the balloon catheter;
 e. inflating the balloon to displace blood inside the vasculature;
 f. infusing a liquid into the infusion space to displace blood between the inflated balloon and the inside wall of the vasculature so as to provide a relatively blood-free interface;
 g. delivering light through the blood-free interface to the vasculature from the light delivery catheter.

2. A method of providing a blood-free interface for intravascular light delivery as in claim 1 wherein the light delivery catheter is inserted into the balloon catheter prior to inserting the balloon catheter into the vasculature of a patient.

3. A method of providing a blood-free interface for intravascular light delivery as in claim 1 wherein the light delivery catheter is inserted into the balloon catheter subsequent to inserting the balloon catheter into the vasculature of a patient.

4. A method of providing a blood-free interface for intravascular light delivery as in claim 1 wherein the light delivery catheter is inserted into the balloon catheter at the same time as the balloon catheter is inserted into the vasculature of a patient.

5. A method of providing a blood-free interface for intravascular light delivery as in claim 1 wherein the balloon is inflated at the same time that fluid is infused into the infusion space.

6. A method of providing a blood-free interface for intravascular light delivery as in claim 1, the method further comprising the steps of:

h. infusing fluid into the working lumen of the balloon catheter and around the light delivery catheter disposed therein.

* * * * *

UNITED STATES PATENT AND TRADEMARK OFFICE
CERTIFICATE OF CORRECTION

PATENT NO. : 5,876,426

DATED : March 2, 1999

INVENTOR(S) : KUME et al.

It is certified that error appears in the above-identified patent and that said Letters Patent is hereby corrected as shown below:

At column 3, line 12, insert --in-- after "illustrated".

At column 4, line 21, "40" should be --40--.

Signed and Sealed this

Seventeenth Day of August, 1999

Attest:

Attesting Officer

Q. TODD DICKINSON

Acting Commissioner of Patents and Trademarks